(12) United States Patent
Davis

(10) Patent No.: US 12,171,890 B2
(45) Date of Patent: Dec. 24, 2024

(54) DISEASE PROTECTION SHEETS

(71) Applicant: Russel Long Davis, Avon, IN (US)

(72) Inventor: Russel Long Davis, Avon, IN (US)

( * ) Notice: Subject to any disclaimer, the term of this patent is extended or adjusted under 35 U.S.C. 154(b) by 550 days.

(21) Appl. No.: 17/679,931

(22) Filed: Feb. 24, 2022

(65) Prior Publication Data

US 2023/0149572 A1    May 18, 2023

Related U.S. Application Data

(60) Provisional application No. 63/279,785, filed on Nov. 16, 2021.

(51) Int. Cl.
| *A61L 2/02* | (2006.01) |
| *A47C 31/11* | (2006.01) |
| *A47K 10/32* | (2006.01) |
| *A47K 10/42* | (2006.01) |
| *A61L 2/24* | (2006.01) |
| *A61L 2/26* | (2006.01) |
| *G08B 21/02* | (2006.01) |

(52) U.S. Cl.
CPC .............. *A61L 2/02* (2013.01); *A47C 31/113* (2013.01); *A47K 10/426* (2013.01); *A61L 2/24* (2013.01); *A61L 2/26* (2013.01); *G08B 21/02* (2013.01); *A47K 2010/3233* (2013.01); *A47K 2010/428* (2013.01); *A61L 2202/14* (2013.01)

(58) Field of Classification Search
CPC ..... A61L 2/02; A61L 2/24; A61L 2/26; A61L 2202/14; A61L 2/232; A47C 31/113; A47C 31/007; A47K 10/426; A47K 2010/3233; A47K 2010/428; G08B 21/02; G08B 21/245
See application file for complete search history.

(56) References Cited

U.S. PATENT DOCUMENTS

| 5,084,927 | A | * | 2/1992 | Parkevich | A47G 9/02 |
| | | | | | 5/939 |
| 10,231,581 | B2 | | 3/2019 | Moskowitz | |
| 10,759,616 | B2 | | 9/2020 | Tran | |
| 11,241,127 | B1 | * | 2/2022 | Briggs | A47K 13/225 |
| 2007/0220664 | A1 | | 9/2007 | Getahun | |
| 2009/0014232 | A1 | * | 1/2009 | Hirsch | A61B 7/02 |
| | | | | | 181/131 |
| 2010/0134296 | A1 | * | 6/2010 | Hwang | G08B 21/245 |
| | | | | | 340/573.1 |
| 2014/0139339 | A1 | * | 5/2014 | Jones | A47K 5/1217 |
| | | | | | 340/573.1 |
| 2017/0027393 | A1 | * | 2/2017 | Barnes | A47K 10/36 |
| 2021/0085136 | A1 | * | 3/2021 | Bartman | A47K 10/3625 |

FOREIGN PATENT DOCUMENTS

EP        1993423 A2    11/2008

* cited by examiner

*Primary Examiner* — Michael Collins

(57) ABSTRACT

The present invention provides device designed to provide sheets that are disposable and water resistant. The present invention includes a plurality of chairs with numbers, a container, sheets having numbers that match one or more of the plurality of numbers attached to the chairs, a chair transceiver and a container transceiver.

20 Claims, 7 Drawing Sheets

DISEASE PROTECTION SHEETS

FIELD OF THE INVENTION

The present invention relates generally to a disposable chair sheet. More specifically, the present invention is related to a device that is designed to properly release sheets that are disposable and water resistant.

BACKGROUND OF THE INVENTION

Maintaining sanitary conditions is important as some diseases such as Covid-19 can be transmitted through tears, sweat, or urine. Therefore, all places, not only hospitals, where new people or patients frequently visit should consider hygiene seriously. Using disposable medical devices and disposable covers for beds and chairs would greatly prevent the diseases from being transmitted.

An objective of the present invention is to provide a sheet that is disposable and water resistant. The plurality of sheets is stored in a container and a user may pull out each sheet at a time. The sheet can be placed on a patient's chair and disposed of after it has been used. Additional features and benefits are further discussed in the sections below.

SUMMARY

In accordance with the present invention, a novel device is provided that requires a plurality of chairs with numbers, a container, sheets having numbers that match one or more of the plurality of numbers attached to the chairs, a chair transceiver and a container transceiver.

In one embodiment, the sheets include a thin layer of square structure. The sheets can be uniform in size, cut and thickness and latex-free.

In some embodiment, the device of the present invention may include codes that indicate a specific command word.

In another embodiment, the container may include a wall mounting bracket.

In yet another embodiment, the container transceiver of the present invention may include a speaker that is configured to make a sound and a light to notify the user that one or more of the sheets are attached to the seat portion of the chair.

DETAIL DESCRIPTIONS OF THE INVENTION

All illustrations of the drawings are for the purpose of describing selected versions of the present invention and are not intended to limit the scope of the present invention.

The present invention provides a sheet that is disposable and water resistant. As some diseases can be transmitted through tears, sweat, or urine, the present invention protects patients, medical staff, and any users from being exposed to the diseases. The sheet may be placed on a chair or any desired object.

Figure 1:
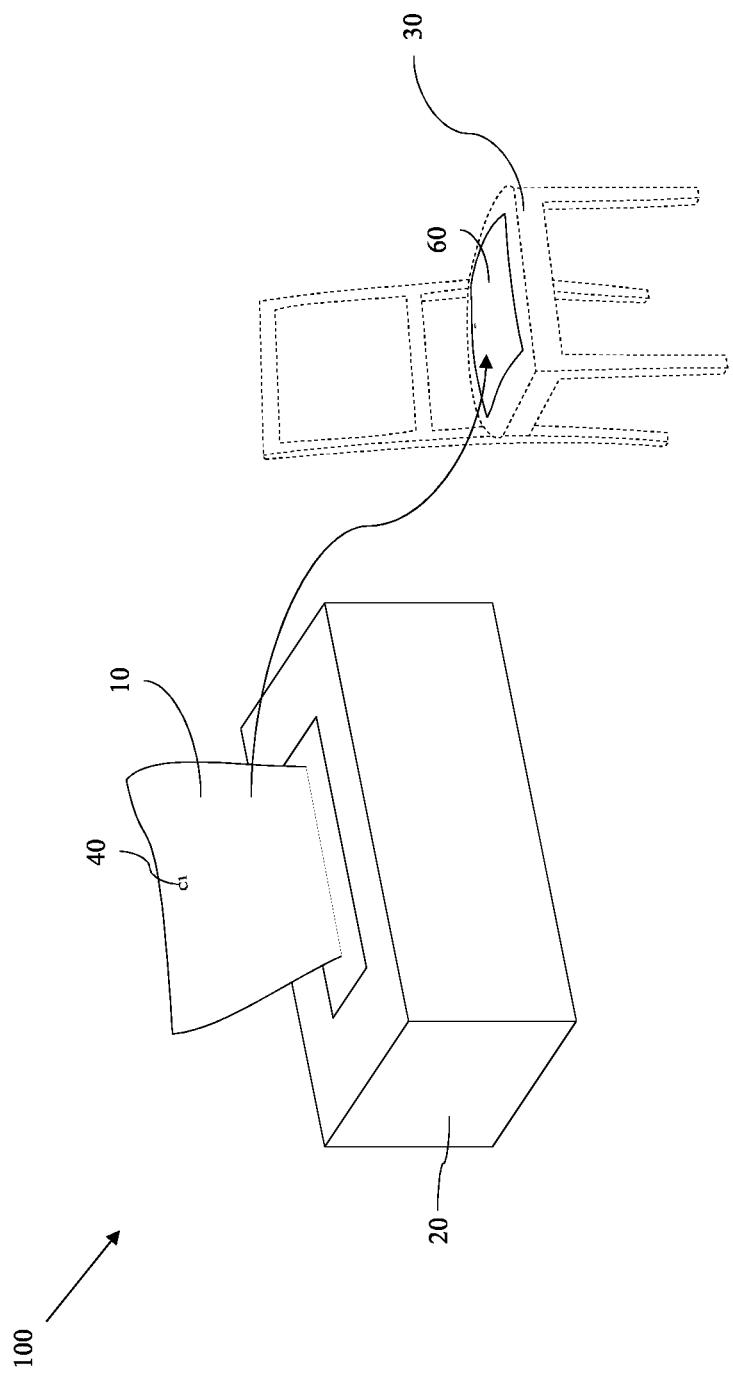
FIG. 1 is an illustration of one embodiment of the present invention.

In a preferred embodiment, as shown in FIG. 1, the present invention comprises a plurality of sheets 10, a container 20, and a plurality of chairs 30. The sheet 10 provides a thin layer of square structure, although any desired shape may be used.

Figure 2:
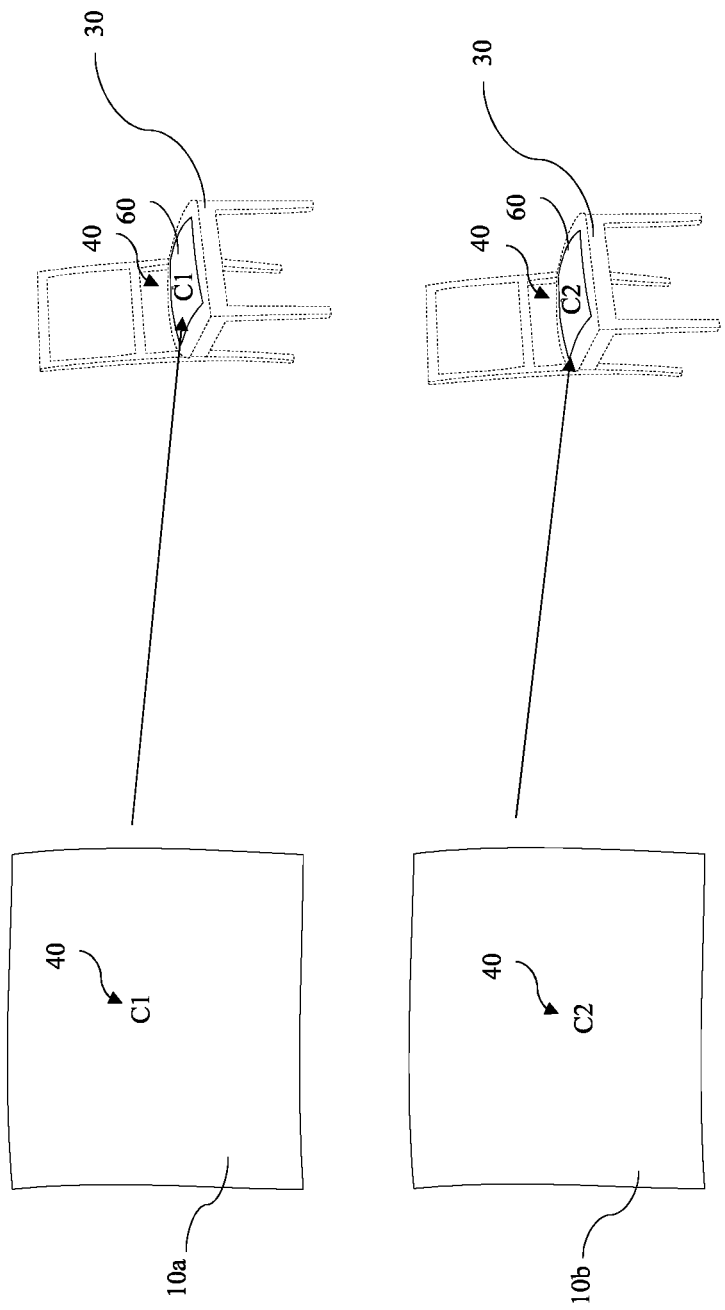
FIG. 2 is an illustration of one embodiment of sheets labeled with unique numbers and designated chairs of the present invention.

In the preferred embodiment, all sheets 10 are labeled with unique numbers 40 or codes (that indicate a specific command word) so that the users can easily find the designated chairs 30. For example, as shown in FIG. 2, the first sheet 10a can be labeled C1, and the next sheet 10b can be labeled C2. The number can change in sequence. The sheet 10 has enough strength against breaking and tearing. In the other embodiment, the sheet 10 is latex-free and uniform in size, cut and thickness. Ins some embodiments, the sheet 10 can be made of disinfectant material for killing bacteria, fungi and viruses.

Figure 3:
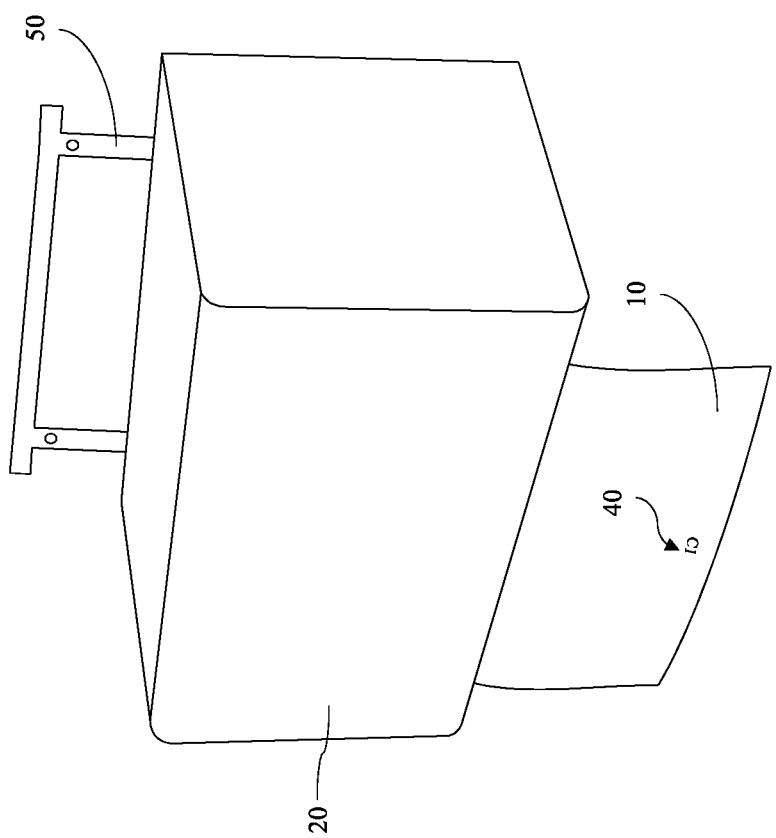
FIG. 3 is an illustration of one embodiment of the container with a mounting bracket of the present invention.

As can be seen in FIG. 3, the plurality of sheets 10 is interfolded and stored in the container 20.

In the preferred embodiment, the container 20 provides a rectangular box structure, although any desired shape or design may be used. As the sheets 10 are interfolded, the next available sheet 10 is dispensed as the user pulls out a sheet 10 from the container 20. As can be seen in FIG. 3, the container 20 can be mounted on a wall using a wall mounting bracket 50.

In the preferred embodiment, each container 20 stores 40 sheets, although any desired amount of sheets 10 may be stored.

In the other embodiments, the sheets 10 and the container 20 are colored and decorated based on the user's preferences. The sheets 10 and the container 20 may be colored for, but not limited to, airlines, cruise ships, hotels, and hospitals.

Figure 4:
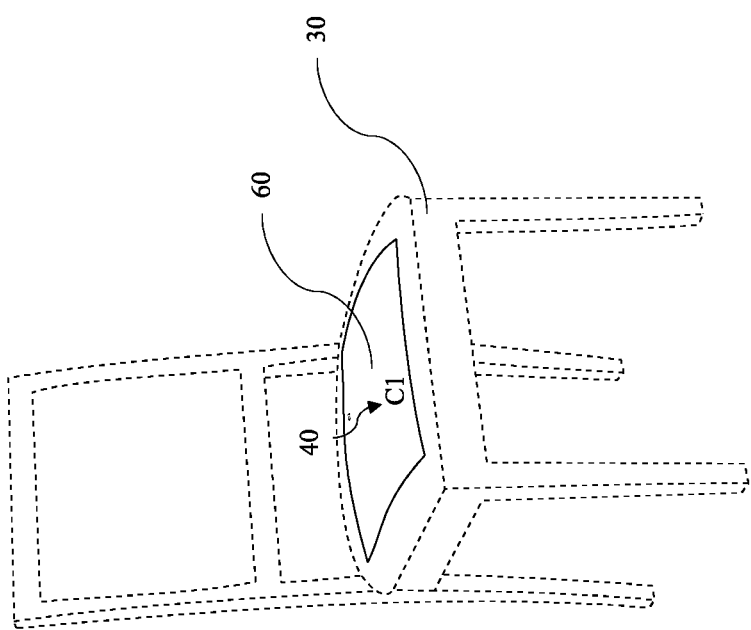
FIG. 4 is an illustration of one embodiment of the chair of the present invention.
Figure 5:
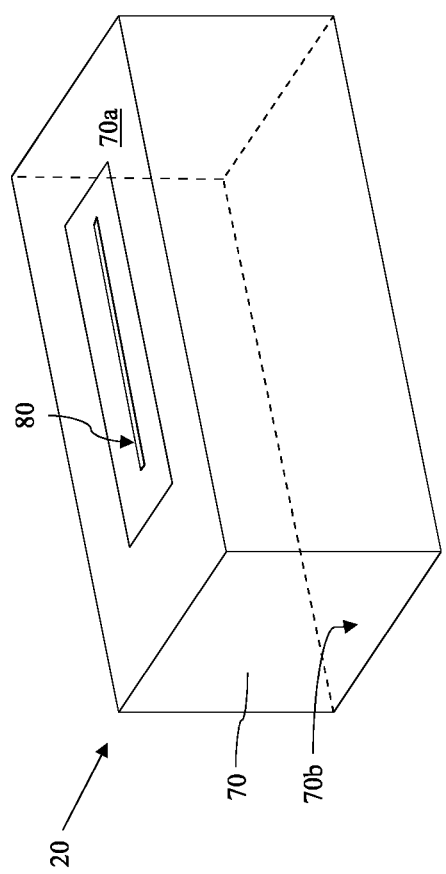
FIG. 5 is an illustration of one embodiment of the container of the present invention.

In one embodiment, as shown in FIG. 4, the present invention may include a plurality of chairs 30 having a plurality of numbers 40 attached to a seat portion 60 of the chairs 30. The container 20 may include a body 70 for holding the plurality of sheets 10 and an opening 80 for removing the sheets from the body 70, as shown in FIG. 5.

In such embodiments, the body 70 of the container 20 may include a first end 70a with the opening 80 positioned substantially in the central area of the first end 70a and a second end 70b.

As described above, the plurality of sheets 10 may include numbers 40 that match one or more of the plurality of numbers 40 attached to the seat portion 60 of the chairs 30.

Figure 6:
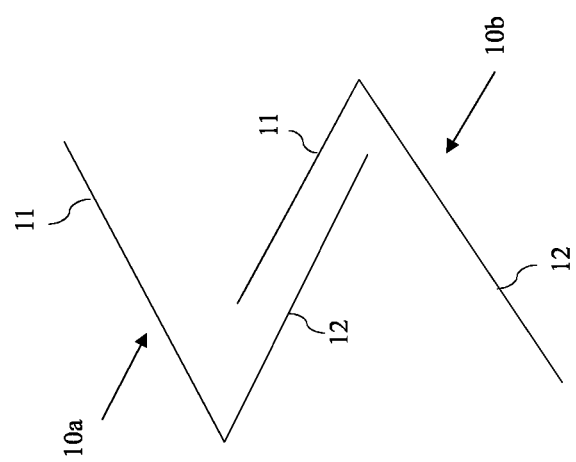
FIG. 6 is an illustration of one embodiment of the sheets of the present invention folding with a leading edge and a trailing edge.

The sheets 10 can be folded in a predetermined pattern and include a leading edge 11 and a trailing edge 12. For example, the sheets 10 can be a rectangular sheet and folded in half as shown in FIG. 6.

In one embodiment, the sheets 10 can be releasably joined together by connecting a trailing edge 12 of a first sheet 10a (which can be the sheet first sheet to be pulled out of the container) and a leading edge 11 of a subsequent sheet (second sheet) 10b so that the user can easily pull the sheet 10 out of the container 20.

Figure 7:
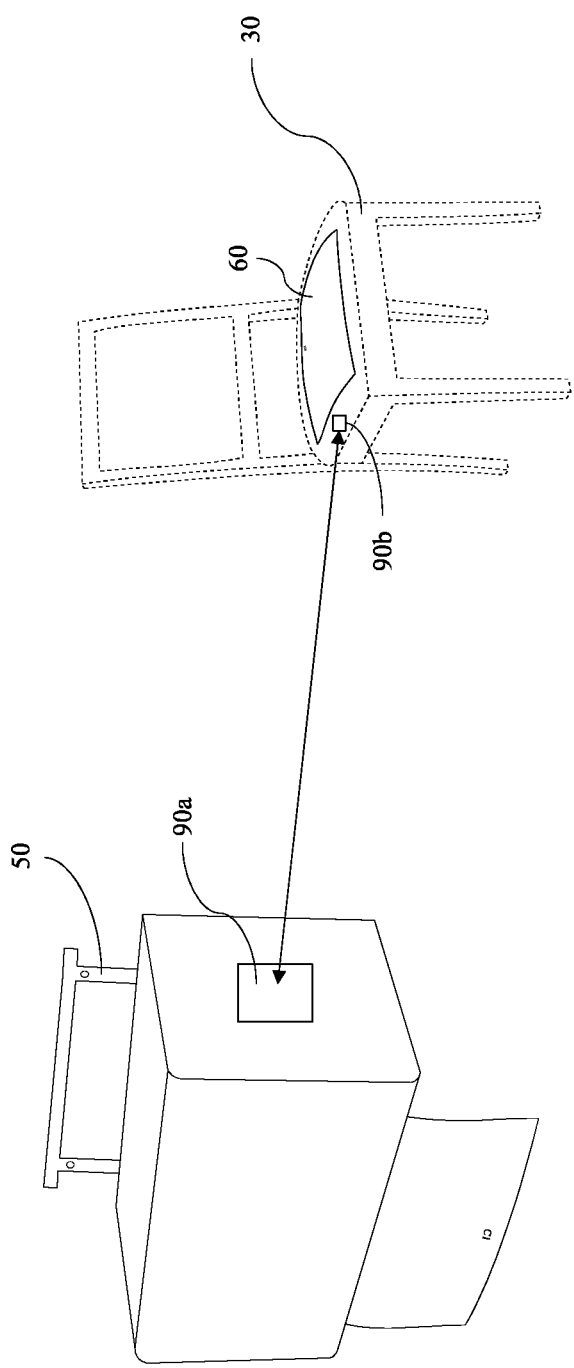
FIG. 7 is an illustration of one embodiment of the present invention showing a chair transceiver and a container transceiver.

In some embodiments, the present invention, as shown in FIG. 7, may include a chair transceiver 90b attached to the plurality of chairs 30. The chair transceiver 90b can be configured to monitor the seat portion 60 of the chair 30 and notify when one or more of the sheets 10 are attached to the seat portion 60 of the chair 30. The present invention may also include a container transceiver 90a attached to the container 20 and communicatively connected to the chair transceiver 90b to notify the user whenever the sheet 10 is placed on the seat portion 60 of the chair 30.

In such embodiments, the container transceiver 90a may include a speaker configured to make a sound and a light source (e.g., LED) configured to emit light when the chair transceiver 90b notifies that one or more of the sheets 10 are attached to the seat portion 60 of the chair 30.

The user can place the sheet 10 on a chair 30. The sheet 10 of the present invention protects the patients or any users from infection bottom leakage from other patients sitting in the chairs 30. The sheet 10 can be easily disposed of after it has been used.

Although the invention has been explained in relation to its preferred embodiment, it is to be understood that many other possible modifications and variations can be made without departing from the spirit and scope of the invention.

What is claimed is:

1. A device comprising:
   a plurality of chairs having a plurality of numbers attached to a seat portion of the chairs;
   a container having a body for holding a plurality of sheets therein and an opening for removing the sheets from the body, the body includes
     a first end with the opening positioned substantially in the central area of the first end,
     a second end,
   the plurality of sheets having numbers that match one or more of the plurality of numbers attached to the seat portion of the chairs, the sheets being folded in a predetermined pattern to have a leading edge and a trailing edge and releasably joined together by connecting a trailing edge of a first sheet and a leading edge of a subsequent sheet;
   a chair transceiver attached to the plurality of chairs, wherein the chair transceiver is configured to notify when one or more of the sheets are attached to the seat portion of the chair; and
   a container transceiver attached to the container and communicatively connected to the chair transceiver.

2. The device as claimed in claim 1, wherein the body includes a rectangular shape.

3. The device as claimed in claim 1, the sheets include a thin layer of square structure.

4. The device as claimed in claim 1, wherein the numbers are codes that indicate a specific command word.

5. The device as claimed in claim 1, wherein the sheets are latex-free.

6. The device as claimed in claim 1, wherein the sheets are made of disinfectant material.

7. The device as claimed in claim 1, wherein the sheets are uniform in size, cut and thickness.

8. The device as claimed in claim 1, wherein the container includes a wall mounting bracket.

9. The device as claimed in claim 1, wherein the container transceiver includes a speaker configured to make a sound when the chair transceiver notifies that one or more of the sheets are attached to the seat portion of the chair.

10. The device as claimed in claim 1, wherein the container transceiver includes a light source configured to emit light when the chair transceiver notifies that one or more of the sheets are attached to the seat portion of the chair.

11. A device comprising:
    a plurality of chairs having a plurality of numbers attached to a seat portion of the chairs;
    a container having a rectangular body for holding a plurality of sheets having a thin layer of square structure, and an opening for removing the sheets from the rectangular body, the rectangular body includes
      a first end with the opening positioned substantially in the central area of the first end,
      a second end,
    the plurality of sheets having numbers that match one or more of the plurality of numbers attached to the seat portion of the chairs, the sheets being folded in a predetermined pattern to have a leading edge and a trailing edge and releasably joined together by connecting a trailing edge of a first sheet and a leading edge of a subsequent sheet;
    a chair transceiver attached to the plurality of chairs, wherein the chair transceiver is configured to notify when one or more of the sheets are attached to the seat portion of the chair; and
    a container transceiver attached to the container and communicatively connected to the chair transceiver.

12. The device as claimed in claim 11, wherein the numbers are codes that indicate a specific command word.

13. The device as claimed in claim 11, wherein the sheets are latex-free.

14. The device as claimed in claim 11, wherein the sheets are made of disinfectant material.

15. The device as claimed in claim 11, wherein the sheets are uniform in size, cut and thickness.

16. The device as claimed in claim 11, wherein the container includes a wall mounting bracket.

17. The device as claimed in claim 11, wherein the container transceiver includes a speaker configured to make a sound when the chair transceiver notifies that one or more of the sheets are attached to the seat portion of the chair.

18. The device as claimed in claim 11, wherein the container transceiver includes a light source configured to emit light when the chair transceiver notifies that one or more of the sheets are attached to the seat portion of the chair.

19. The device as claimed in claim 11, wherein the container transceiver includes a speaker configured to make a sound and a light source configured to emit light when the chair transceiver notifies that one or more of the sheets are attached to the seat portion of the chair.

20. A device comprising:
    a plurality of chairs having a plurality of numbers attached to a seat portion of the chairs, wherein the numbers are codes that indicate a specific command word;
    a container having a rectangular body for holding a plurality of sheets having a thin layer of square structure, and an opening for removing the sheets from the rectangular body, the rectangular body includes
      a first end with the opening positioned substantially in the central area of the first end,
      a second end,
    the plurality of sheets having numbers that match one or more of the plurality of numbers attached to the seat portion of the chairs, the sheets being folded in a predetermined pattern to have a leading edge and a trailing edge and releasably joined together by connecting a trailing edge of a first sheet and a leading edge of a subsequent sheet;
    a chair transceiver attached to the plurality of chairs, wherein the chair transceiver is configured to notify when one or more of the sheets are attached to the seat portion of the chair; and a container transceiver attached to the container and communicatively connected to the chair transceiver.

* * * * *